United States Patent
Kim et al.

(10) Patent No.: US 9,551,025 B2
(45) Date of Patent: Jan. 24, 2017

(54) NUCLEIC ACID STRUCTURE COMPLEX INCLUDING NUCLEIC ACIDS, RAMAN-ACTIVE MOLECULES, AND METAL PARTICLES, METHOD OF PREPARING THE SAME, AND METHOD OF DETECTING TARGET MATERIAL BY USING THE NUCLEIC ACID STRUCTURE COMPLEX

(71) Applicant: Samsung Electronics Co., Ltd., Suwon-si, Gyeonggi-do (KR)

(72) Inventors: Myoung-soon Kim, Seoul (KR); Jong-myeon Park, Incheon (KR); Jung-won Keum, Seoul (KR); Chang-eun Yoo, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 192 days.

(21) Appl. No.: 14/067,825

(22) Filed: Oct. 30, 2013

(65) Prior Publication Data

US 2014/0120629 A1    May 1, 2014

(30) Foreign Application Priority Data

Oct. 30, 2012 (KR) .................. 10-2012-0121545
Nov. 27, 2012 (KR) .................. 10-2012-0135563
Sep. 4, 2013 (KR) .................. 10-2013-0106312

(51) Int. Cl.
*C07H 21/02* (2006.01)
*C12Q 1/68* (2006.01)
*G01N 33/53* (2006.01)
*G01N 33/566* (2006.01)
*C07H 21/04* (2006.01)
*C07K 16/00* (2006.01)

(52) U.S. Cl.
CPC ......... *C12Q 1/6816* (2013.01); *G01N 33/5308* (2013.01)

(58) Field of Classification Search
None
See application file for complete search history.

(56) References Cited

U.S. PATENT DOCUMENTS 7,259,252 B2    8/2007    Mirkin et al.
8,003,408 B2    8/2011    Zhang et al.
(Continued)

FOREIGN PATENT DOCUMENTS

KR    1020090017434 A    2/2009
KR    1020090030767 A    3/2009
(Continued)

OTHER PUBLICATIONS

Chen et al., "DNA-based plasmonic nanoarchitectures: from structural design to emerging applications", *WIREs Nanomed Nanobiotechnol*, 4, 587-604, doi: 10.1002/wnan.1184 (2012).
(Continued)

*Primary Examiner* — Joseph G Dauner
(74) *Attorney, Agent, or Firm* — Leydig, Voit & Mayer, Ltd.

(57) ABSTRACT

Provided are nucleic acid structures suitable for reproducible Raman spectroscopy, methods of preparing the same, and methods of detecting a target material using the nucleic acid structures, whereby various target materials may be analyzed by using reproducible Raman spectroscopy.

17 Claims, 11 Drawing Sheets

(56) References Cited

U.S. PATENT DOCUMENTS

2006/0228725 A1* 10/2006 Salafsky ............... B82Y 30/00
                                              435/6.11
2009/0227774 A1*  9/2009 Turberfield ........ C12N 15/1031
                                              530/358
2013/0330839 A1  12/2013 Suh et al.

FOREIGN PATENT DOCUMENTS

KR    1020110039688 A    4/2011
KR      2012-0056024 A    6/2012

OTHER PUBLICATIONS

Graham et al., "Biosensing using silver nanoparticles and surface enhanced resonance Raman scattering," *Chem. Commun*, 4363-4371 (2006).
Lim et al., "Nanogap-engineerable Raman-active nanodumbbells for single-molecule detection," *Nature Materials*, 9: 60-67 (2010).
Mastroianni et al., "Pyramidal and Chiral Groupings of Gold Nanocrystals Assembled Using DNA Scaffolds," *J. Am. Chem. Soc*, 131(24), 8455-8459 (2009).

* cited by examiner

DNA STRUCTURE

▬▬▬ REPORTER
● : FUNCTIONAL GROUP FOR FIXING
   TARGET NUCLEIC ACID TO A SUPPORT

SEQUENCE LISTING

```
<160> NUMBER OF SEQ ID NOS: 4

<210> SEQ ID NO 1
<211> LENGTH: 62
<212> TYPE: DNA
<213> ORGANISM: Artificial Sequence
<220> FEATURE:
<223> OTHER INFORMATION: Synthetic (nucleotide for manufacturing a
      nucleic acid structure)

<400> SEQUENCE: 1
tcccatgtgt ctcgtcgtaa attatatcat tcggacgttc cagcttccct gttaagttct     60
ac                                                                    62

<210> SEQ ID NO 2
<211> LENGTH: 62
<212> TYPE: DNA
<213> ORGANISM: Artificial Sequence
<220> FEATURE:
<223> OTHER INFORMATION: Synthetic (nucleotide for manufacturing a
      nucleic acid structure)

<400> SEQUENCE: 2
ttacgacgag acacatggga accgaacaat gtcggaacgg caggccaatg ctcacggcgg     60
```

-continued

```
ag                                                              62

<210> SEQ ID NO 3
<211> LENGTH: 62
<212> TYPE: DNA
<213> ORGANISM: Artificial Sequence
<220> FEATURE:
<223> OTHER INFORMATION: Synthetic (nucleotide for manufacturing a
      nucleic acid structure)

<400> SEQUENCE: 3
ggaacgtccg aatgatataa actccgccgt gagcattggc catgaaactc ccagcgagca    60
gc                                                              62

<210> SEQ ID NO 4
<211> LENGTH: 62
<212> TYPE: DNA
<213> ORGANISM: Artificial Sequence
<220> FEATURE:
<223> OTHER INFORMATION: Synthetic (nucleotide for manufacturing a
      nucleic acid structure)

<400> SEQUENCE: 4
gccgttccga cattgttcgg agtagaactt aacagggaag cagctgctcg ctgggagttt    60
ca                                                              62
```

NUCLEIC ACID STRUCTURE COMPLEX INCLUDING NUCLEIC ACIDS, RAMAN-ACTIVE MOLECULES, AND METAL PARTICLES, METHOD OF PREPARING THE SAME, AND METHOD OF DETECTING TARGET MATERIAL BY USING THE NUCLEIC ACID STRUCTURE COMPLEX

CROSS-REFERENCE TO RELATED APPLICATIONS

This application claims the benefit of Korean Patent Application No. 10-2012-0121545, filed on Oct. 30, 2012, Korean Patent Application No. 10-2012-0135563, filed on Nov. 27, 2012 and Korean Patent Application No. 10-2013-0106312, filed on Sep. 4, 2013, in the Korean Intellectual Property Office, the entire disclosures of which are incorporated herein by reference.

BACKGROUND

1. Field

The present disclosure relates to nucleic acid structure complexes suitable for Raman spectroscopy, methods of preparing the same, and methods of detecting target materials by using the nucleic acid structure complexes.

2. Description of the Related Art

Raman scattering is the inelastic scattering of photons wherein the energy of incident light is changed, and denotes a phenomenon where, when light is incident on a predetermined molecular sieve, light having a wavelength slightly different from that of the incident light is generated due to a unique vibrational transition of the molecular sieve. However, despite the fact that Raman spectroscopy has many possible applications, Raman spectroscopy devices have not been commercialized to date because Raman spectroscopy has weak signal intensity and low reproducibility.

A method of overcoming such limitations may be surface enhanced Raman scattering or surface enhanced Raman spectroscopy (SERS), which involves repeated oxidation-reduction of a silver electrode and adsorbtion of pyridine molecules thereon in an aqueous solution. An increase in signal intensity of about $10^6$ times has been observed by SERS. However, SERS may be pose difficulties with regard to synthesis and control of a nanomaterial accurately and structurally defined. Since there are many limitations in terms of reproducibility and reliability, research into applying SERS has been conducted.

SUMMARY

Provided are nucleic acid structure complexes useful in Raman spectroscopy, as well as methods of preparing the nucleic acid structure complexes.

Also provided are methods of detecting target materials by using the nucleic acid structure complexes.

Additional aspects will be set forth in part in the description which follows and, in part, will be apparent from the description, or may be learned by practice of the presented embodiments.

In one aspect, the nucleic acid structure complex includes: a nucleic acid including a hybridization region in which a single strand and a single strand are hybridized, such that the hybridization region is double stranded; one or more Raman-active molecules attached to or otherwise included in the nucleic acid structure complex; and one or more metal particles attached to or otherwise included in the nucleic acid structure complex.

Raman scattering refers to a phenomenon in which, when light passes through a certain medium, a portion of the light deviates from a passing direction and progresses in a different direction. The term "SERS" (surface enhanced Raman spectroscopy or surface enhanced Raman scattering) refers to a phenomenon in which, when a molecule is located around a metal nanostructure, the intensity of Raman scattering of the molecule is significantly increased.

The nucleic acid structure complex includes a nucleic acid structure that may be prepared from one or more oligonucleotides. Nucleic acids constituting the nucleic acid structure may include a hybridization region in which two single stranded nucleic acids are hybridized, thereby providing a double stranded region. The double-stranded nucleic acid may be formed through hybridization of an oligonucleotide with itself (e.g., a single oligonucleotides chain folded over onto itself at hybridization regions) or hybridization with other oligonucleotides (two or more oligonucleotides chains associated into a single structure by hybridization at hybridization regions). An oligonucleotide of the nucleic acid structure may include one or more hybridization regions. A single oligonucleotide may include the plurality of hybridization regions, and may be hybridized to multiple (two or more, three or more, four or more, etc.) other oligonucleotides. Furthermore, oligonucleotides of the nucleic acid structure may be hybridized with a hybridization region of one or more other oligonucleotides chains that are identical and/or different.

The nucleic acid structure may be self-assembled. The term "self-assembly" denotes a phenomenon in which a nanostructure is spontaneously formed by covalent or non-covelant bonds between atoms, or other types of molecular interaction, to form a particular structure. The one or more oligonucleotides may include one or more sequences or regions that are complementary to and, thus, hybridizable with, the sequences of other oligonucleotides. The nucleic acids may, therefore, be self-assembled through hybridization between complementary sequences.

The nucleic acid structure may be a polyhedron formed from nucleic acids in the nucleic acid structure complex. The polyhedron may be a nucleic acid polyhedron; in other words, the nucleic acid structure comprising one or more oligonucleotide chains hybridized to one another is configured as a polyhedron. The nucleic acid polyhedron may be designed to have a predetermined number of faces, edges, and/or vertices. The nucleic acid polyhedron may have a plurality of faces, edges, and/or vertices (e.g., at least two or more, at least three or more, at least four or more, etc., faces, edges, and/or vertices). At least a portion of each edge of the nucleic acid polyhedron may be provided by a double-stranded nucleic acid (e.g., a hybridization region). In some embodiments, most of each edge of the nucleic acid polyhedron may be provided by a double-stranded nucleic acid, or the entire portion of the each edge may be provided by a double-stranded nucleic acid. For example, the nucleic acid polyhedron may have 4, 5, 6, 7, 8, 9, 10, 11, 12, 13, 14, or 14 or more edges or faces. The nucleic acid polyhedron, for example, may be a tetrahedron, a hexahedron, a pyramid, a dipyramid, or an octahedron. The nucleic acid polyhedron may be a regular polyhedron or an irregular polyhedron. The nucleic acid polyhedron may be rigid. In the nucleic acid structure, each oligonucleotide constituting the nucleic acid structure may be self-assembled to allow the 5' end and/or 3' end (terminus) of the each oligonucleotide to be disposed on the vertices of the nucleic acid polyhedron. The polyhedron may be one selected from the group consisting of a tetrahedron, an octahedron, a dodecahedron, a trigonal bipyramid, and a bipyramid. The nucleic acid structure may be selected to have a predetermined size. The size of the nucleic acid structure may be selected based on a size of the individual oligonucleotides chains and the size of the hybridization regions. In some embodiments, an edge of the nucleic acid polyhedron may have, for instance, a length of 5 or more, 10 or more, 20 or more, 30 or more, 40 or more, or 50 or more nucleotides or base pairs.

The nucleic acid structure may include nucleic acids selected from the group consisting of deoxyribonucleic acids (DNAs), ribonucleic acids (RNAs), peptide nucleic acids (PNAs), locked nucleic acids (LNAs), nucleic acid-like structures, a combination thereof, and an analogue thereof. The nucleic acid structure may include nucleotide analogues having bonding properties similar to or better than those of a naturally occurring nucleotide. The nucleic acid structure may include a nucleic acid analogue having a synthetic backbone. The synthetic backbone analogue may include phosphodiester, phosphorothioate, phosphorodithioate, methyl phosphonate, phosphoramidate, alkyl phosphotriester, sulfamate, 3'-thioacetal, methylene(methylimino), 3'-N-carbamate, morpholino carbamate, PNAs, modified phosphodiester, or modified methylphosphonate bonds. The nucleic acid (e.g., DNA) used for preparing the nucleic acid structure may be naturally occurring, modified, or synthetic nucleic acid.

The nucleic acid structure may be detectably labeled. The label may include a fluorescent molecule, a radioactive isotope, an enzyme, an antibody, or other detectable moiety.

The term "linker compound" denotes a compound connected to the sequence of each oligonucleotide for attaching the oligonucleotides to the metal particles. The linker compound may be connected to the 5' end and/or 3' end of the each oligonucleotide. Methods of bonding the metal particles to the oligonucleotides through the linker compound are known in the art. One end of the linker compound may consist of or comprise a functional group attachable to surfaces of the metal particles. For example, the functional group may be a sulfur-containing group including a thiol group or a sulfhydryl group. The functional group may be an alcohol and/or phenol derivative, and may be a compound having a formula of RSH containing sulfur in an oxygen site, wherein R is substituted or unsubstituted alkyl, cyclic or heterocyclic aromatic group, or aliphatic group. Also, the functional group may be thiol ester or dithiol ester having a formula of RSR' or RSSR', respectively, wherein R and R' are independently substituted or unsubstituted alkyl, cyclic or heterocyclic aromatic group, or aliphatic group. Further, the functional group may be an amino group ($-NH_2$) or carboxyl group. The metal particles may be attached to the nucleic acid structure through the linker compound. The metal particles may be attached to the vertices of the nucleic acid structure through the linker compound, for instance, when the linker compound is connected to the 5' end and/or 3' end of the each oligonucleotides and the 5' and/or 3' end of the oligonucleotides are positioned at the vertices of the nucleic acid structure.

The nucleic acid structure complex may include one or more metal particles. The metal particles may be optically active molecules. The metal particles may be selected from the group consisting of gold (Au), silver (Ag), copper (Cu), sodium (Na), aluminum (Al), chromium (Cr), platinum (Pt), ruthenium (Ru), palladium (Pd), iron (Fe), cobalt (Co), nickel (Ni), and a combination thereof. The metal particles may be metal nanoparticles. Also, metal ions or metal ion chelates may be used. The metal particles may be chemically reduced or subjected to laser ablation.

The nucleic acid structure complex may include one or more signal materials. The signal material used in the present invention may include a colorable marker encompassing Raman-active molecules, fluorescent organic molecules, non-fluorescent organic molecules, and inorganic nanoparticles. The term "Raman-active molecules" used in the present invention denotes molecules facilitating the detection and measurement of analytes by a Raman detection instrument when nanoparticles of the present invention are attached to one or more analytes. The Raman-active molecules may include surface enhanced Raman-active molecules, surface-enhanced resonance Raman-active molecules, hyper Raman-active molecules, or coherent anti-Stokes Raman-active molecules. The Raman-active molecules may generate sharp spectrum peaks. The Raman-active molecules may include Raman-active tags. The Raman-active molecules may be selected from the group consisting of cyanine, fluorescein, rhodamine, 7-nitrobenz-2-oxa-1,3-diazole (NBD), phthalic acid, terephthalic acid, isophthalic acid, cresyl fast violet, cresyl blue violet, brilliant cresyl blue, para-aminobenzoic acid, erythrosine, biotin, digoxigenin, phthalocyanine, azomethine, xanthine, N,N,-diethyl-4-(5'-azobenzotriazolyl)-phenylamine, aminoacridine, and a combination thereof. Examples of the cyanine may be Cy3, Cy3.5, or Cy5. Examples of the fluorescein may be carboxyfluorescein (FAM), 6-carboxy-2',4,4', 5',7,7'-hexachlorofluorescein (HEX), 6-carboxy-2',4,7,7'-tetrachlorofluorescein (TET), 5-carboxy-4',5'-dichloro-2',7'-dimethoxyfluorescein, 6-carboxy-4',5'-dichloro-2',7'-dimethoxyfluorescein (Joe), 5-carboxy-2',4',5',7'-tetrachlorofluorescein, 5-carboxyfluorescein, or succinylfluorescein. Examples of the rhodamine may be tetramethylrhodamine (Tamra), 5-carboxyrhodamine, 6-carboxyrhodamine, rhodamine 6G (R6G), tetramethyl rhodamine isothiol (TRIT), sulforhodamine 101 acid chloride (Texas Red dye), carboxy-X-rhodamine (Rox), or rhodamine B.

The nucleic acid structure complex may further comprise a targeting moiety that specifically binds a target material. In the nucleic acid structure complex, a target material may be bonded to the surfaces of the metal particles or the targeting moiety. The target material may be formed of organic molecules, inorganic molecules, or biomolecules. Examples of the target material include amino acids, peptides, polypeptides, proteins, carbohydrates, fatty acid, lipids, nucleotides, oligonucleotides, polynucleotides, glycoproteins, such as prostate specific antigen (PSA), proteoglycans, lipoproteins, lipopolysaccharides, drugs, drug metabolites, small organic molecules, inorganic molecules and natural or synthetic polymers. Examples of target material include glucose, free fatty acids, lactic acid, C-reactive protein and anti-inflammatory mediators, such as cytokines, eicosanoids, or leukotrienes. The biomolecules may be a protein, a nucleic acid, a sugar, or a combination thereof. The biomolecules may be pathogens.

In the nucleic acid structure complex, the oligonucleotide may further include a functional group that binds a target, or an oligonucleotide having a sequence complementary to target nucleic acid. The functional group may be for binding to a first material, which in turn binds to a target material. The target material is thereby bound to the nucleic acid structure complex. The functional group may be attached to one end of the oligonucleotide. For example, the functional group may be a sulfur-containing group including a thiol group or a sulfhydryl group. The functional group may be an alcohol and/or phenol derivative, and may be a compound having a formula of RSH. Also, the functional group may be thiol ester or dithiol ester having a formula of RSR' or RSSR', respectively. Further, the functional group may be an amino group or carboxyl group. The functional group may protrude from a face or vertex of the nucleic acid structure complex. The oligonucleotide having a sequence complementary to a target nucleic acid may be hybridized with a portion of sequences of oligonucleotides constituting the target nucleic acid included in the target material.

A material bondable to the target material may specifically bind to a target material. Specific binding refers, for example, to the binding of a ligand and a receptor or the like, such as the binding of an antibody to an antigen, a receptor to a ligand, or an enzyme to a substrate or an inhibitor. The material that specifically binds to the target material is a material bondable to a nucleic acid According to another aspect of the present invention, a method of preparing a nucleic acid structure complex includes: providing one or more oligonucleotides chains including one or more pairs of complementary nucleotide sequences; hybridizing the complementary sequences of the one or more oligonucleotides chains to form a polyhedral nucleic acid structure; and attaching metal particles to the nucleic acid structure.

All aspects of the nucleic acid structure complex are as hereinabove described. Thus, descriptions related to the nucleic acid structure, the metal particles, the Ramen active molecules, etc., are the same as those described with regard to the nucleic acid structure complex of the invention.

Hybridizing the complementary sequences of the one or more oligonucleotides chains to form a polyhedral nucleic acid structure may be accomplished by combining the one or more oligonucleotides in a suitable medium that will allow the complementary sequences to hybridize. The complementary sequences and their respective position and orientation in the oligonucleotides are designed to providing the polyhedral structure upon hybridization. In other words, the nucleic acid structure may be self-assembled.

The metal particles may be attached to the nucleic acid structure complex by any suitable method. For instance, the oligonucleotides used to provide the nucleic acid structure can be modified to include functional groups that bind metal particles. The functional groups can be positioned, for instance, at the 3' and/or 5' terminus of the oligonucleotides. Furthermore, the 3' and 5' terminus of the oligonucleotides can be located at the vertices of the polyhedral structure. The method of preparing a nucleic acid structure complex may further include reducing the metal particles. The metal particles may be chemically reduced or subjected to laser ablation.

The method may further include providing a Ramen-active molecule in the complex. A Raman-active molecule may be attached to the oligonucleotides, for instance, by synthesizing the oligonucleotides using a modified nucleotide residue that comprises a Ramen-active molecule, thereby incorporating the Ramen-active molecule into the oligonucleotide chain.

According to another aspect of the present invention, a method of detecting a target material includes: exposing a nucleic acid structure complex as described herein to a sample including a target material; and detecting a Raman signal by using Raman spectroscopy.

In the exposing of the nucleic acid structure complex to a sample including a target material, any sample may be used so long as the sample includes the target material. The target material may be a biologically or non-biologically derived material. The biologically derived material may be a material derived from a virus or organism. The biologically derived material may include a cell or the components thereof. The cell may include a eukaryotic cell or a prokaryotic cell. For example, the cell may be a gram-positive or gram-negative bacterial cell. Components of the biological cell may be a protein, a glycolipid, a nucleic acid, or a combination thereof. The sample may include a biological material. The sample, for example, may be blood, urine, a mucous membrane, saliva, a body fluid, a tissue, a biopsy material, or a combination thereof.

In the detecting of the Raman signal by using Raman spectroscopy, the Raman spectroscopy may be surface enhanced Raman spectroscopy (SERS), surface-enhanced resonance Raman spectroscopy (SERRS), hyper Raman spectroscopy, or coherent anti-Stokes Raman spectroscopy (CARS).

The nucleic acid structure complex may further include a first material that binds to a target material. The material that binds to a target material may be attached to the complex by way of a functional group. Descriptions related to the functional group are the same as the foregoing descriptions. The first material that binds to a target material may include an amino group or carboxyl group. For instance, the first material may be an amino acid, a protein, or an antibody.

The method may further include exposing the oligonucleotide including a region hybridizable with a target nucleic acid to a sample including the target nucleic acid. The oligonucleotide including a region hybridizable with a target nucleic acid may be hybridized with the target nucleic acid to form a double-stranded nucleic acid.

The method may further include exposing a sample including a target material to a support including a second material bondable to the target material. The support may have a functional group having hydrogen bond donating ability, wherein the hydrogen binding activity may be due to the characteristics of a substrate material or to characteristics of a functional group added by a chemical or physical treatment, such as a coating. The functional group may be biotin. The second material may be a compound derived from an organism, and for example, may be selected from the group consisting of a nucleic acid, a protein, a polysaccharide, and molecules formed of a combination thereof. DNA or RNA may be included in the nucleic acid. The second material may specifically react with a target material to be analyzed. For example, when the second material is a nucleic acid, the second material may interact with a target nucleic acid having a complementary nucleotide sequence through a hybridization reaction. When the second material is a protein, the second materials may specifically interact with each other through antigen and antibody reactions, interactions between a ligand and a receptor, or interactions between an enzyme and a substrate. Also, when the second material is a polysaccharide, the second material may be specifically recognized by a protein or an antibody, such as lectin recognizing a polysaccharide.

The exposing may further include injecting the nucleic acid structure into the support. The nucleic acid structure may be specifically bonded to the target material fixed to the support.

The method may further include separating the nucleic acid structure complex and any bound target material from the sample prior to detecting a Raman Signal. Separation may be performed, for instance, by washing the sample. When a solid support is used, the method may further include washing the target material bonded to the support such as solid support. The washing method may be performed by removing a material not bonded or a material weakly bonded to the support, while not substantially removing the target material bonded to the support. A washing solution or condition may be appropriately selected by a person skilled in the art.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Hereinafter, the present invention will be described in detail according to exemplary embodiments. However, the following embodiments are merely presented to exemplify the present invention, and the scope of the present invention is not limited thereto. As used herein, the term "and/or" includes any and all combinations of one or more of the associated listed items. Expressions such as "at least one of," when preceding a list of elements, modify the entire list of elements and do not modify the individual elements of the list.

Figure 1:
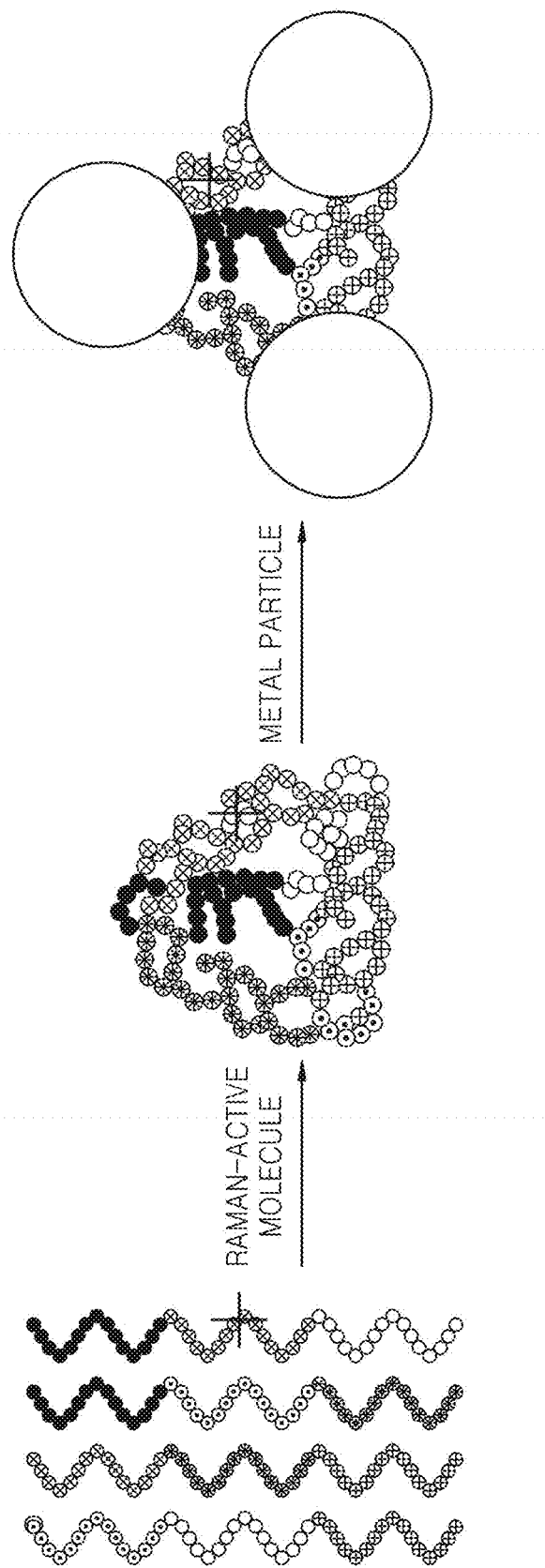
FIG. 1 is a diagram that illustrates a method of preparing a deoxyribonucleic acid (DNA) structure, metal particles, and Raman-active molecules according to an exemplary embodiment.

FIG. 1 illustrates a method of preparing a deoxyribonucleic acid (DNA) structure, metal particles, and Raman-active molecules according to an exemplary embodiment.

Referring to FIG. 1, four oligonucleotides including complementary nucleotide sequences 1-6 may be provided. The oligonucleotide may include a Raman-active molecule. The oligonucleotide may include the Raman-active molecule in the inside thereof. The oligonucleotide may include the Raman-active molecule between nucleotides. The Raman-active molecule may include a surface enhanced Raman-active molecule. The oligonucleotide may include a linker compound (not shown).

The oligonucleotide may include one or more hybridization regions. The hybridization region may include a region in which two single strands are hybridized or may be hybridized. A DNA tetrahedron may be formed by hybridization of the oligonucleotide. The oligonucleotide may be self-assembled through the hybridization to form the DNA tetrahedron.

A nucleic acid structure complex may be prepared by attaching metal particles such as gold particles to the DNA tetrahedron thus formed. Gold particles may be attached to the DNA tetrahedron through the linker compound included in the oligonucleotides constituting the DNA tetrahedron. Since the distance between hot spots generating a strong electromagnetic field in a localized region may be controlled by using a rigid DNA structure, a reproducibly intensified Raman signal may be obtained.

Figure 2:
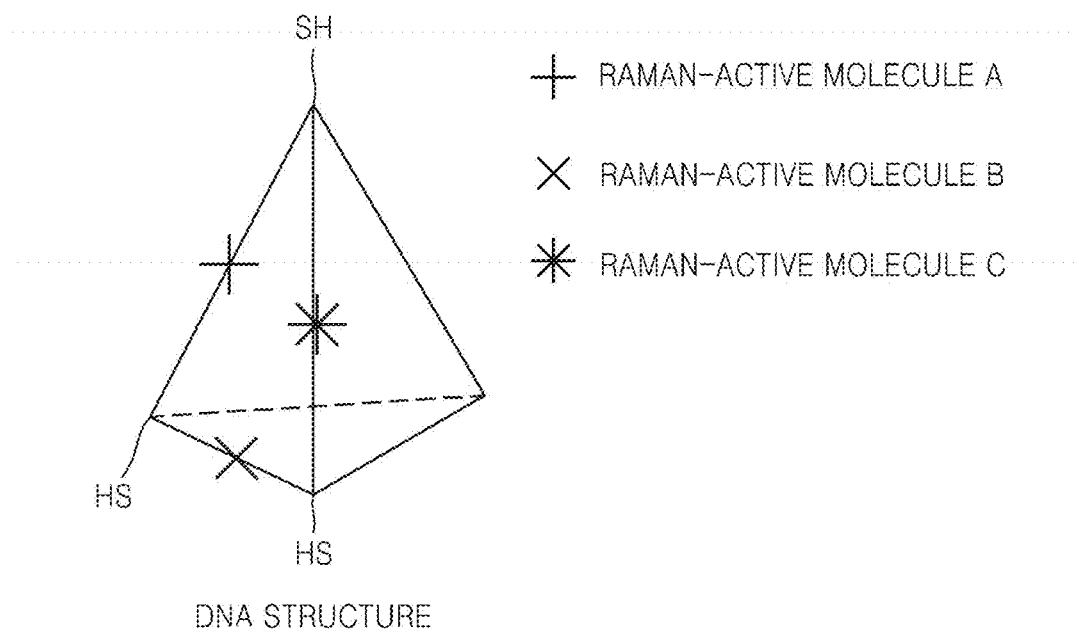
FIG. 2 is a schematic view illustrating a DNA structure including Raman-active molecules according to an exemplary embodiment.

FIG. 2 is a schematic view illustrating a DNA structure including Raman-active molecules according to an exemplary embodiment. Referring to FIG. 2, Raman-active molecules A, B, and C may be all introduced into the DNA structure. Since the Raman-active molecules may be introduced into the oligonucleotides constituting the DNA structure, the Raman-active molecules may be introduced into any region of the DNA structure. Also, the number of introducible Raman-active molecules may vary. Gold particles may be attached to the DNA tetrahedron through the linker compound containing sulfide included in the oligonucleotides constituting the DNA tetrahedron. Gold particles may be attached to the DNA tetrahedron through the linker compound containing —SH included in the oligonucleotides constituting the DNA tetrahedron. The —SH may be —SH bonded to hydrocarbon. The —SH may include —(SH)$_2$. The gold particles may be attached to vertices of the DNA tetrahedron where the linker compounds containing —SH are disposed. The linker compound containing —SH may be a dithiol group.

Figure 3:
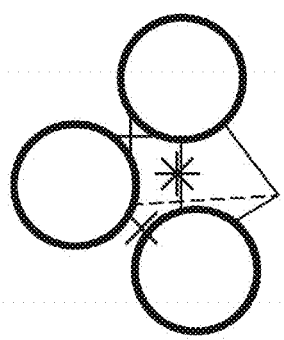
FIG. 3 is a schematic view illustrating a nucleic acid structure complex according to an exemplary embodiment.

FIG. 3 is a schematic view illustrating a nucleic acid structure complex according to an exemplary embodiment. Referring to FIG. 3, metal particles may be attached to the vertices of the DNA tetrahedron including Raman-active molecules. Bonding between the DNA structure and the metal particles may be performed through a linker compound. The linker compound may be connected to any position of the oligonucleotides constituting the DNA structure. The metal particles may be attached to a position in which the linker compound introduced into the oligonucleotides is disposed.

Figure 4:
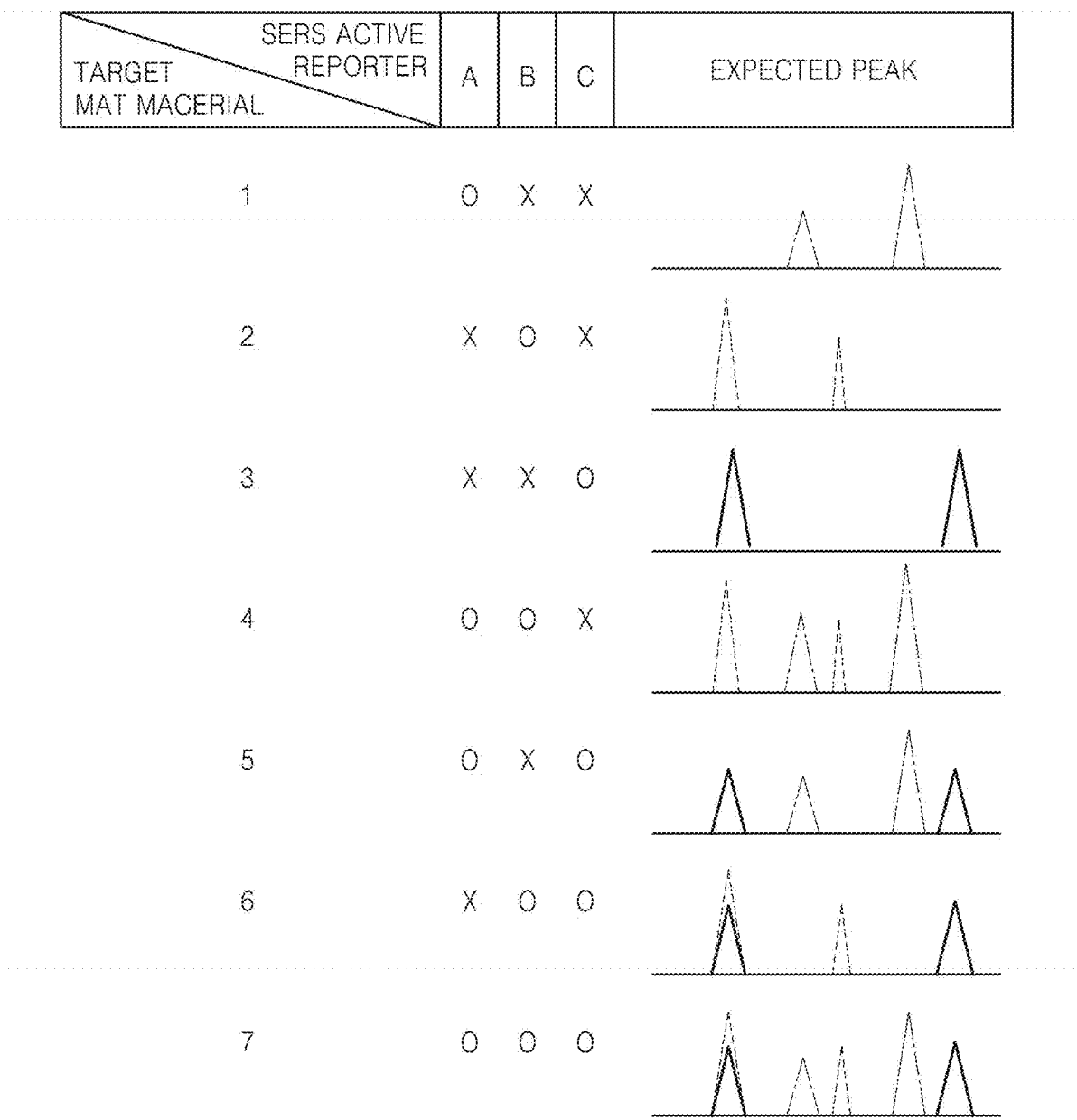
FIG. 4 is a diagram that illustrates that surface enhanced Raman spectroscopy (SERS) measurements may be performed by introducing various types of Raman-active molecules according to an exemplary embodiment.

FIG. 4 illustrates that surface enhanced Raman spectroscopy (SERS) measurements may be performed by introducing various types of Raman-active molecules according to an exemplary embodiment. Referring to FIG. 4, a total of seven target materials may be identified by introducing three types of Raman-active molecules, SERS active reporters. Since the number of the Raman-active molecules introducible into the nucleotides constituting the nucleic acid structure may vary, many types of target materials may be simultaneously identified. The Raman-active molecules may generate sharp spectrum peaks. Since the Raman-active molecules have narrow half widths, various Raman-active molecules may be simultaneously used. Also, $2^{n-1}$ multiple Raman signals may be generated by introducing n Raman-active molecules into a nucleic acid structure complex. Therefore, the nucleic acid structure complex having the n Raman-active molecules may function to identify various target materials by generation of multiple Raman signals.

Figure 5:
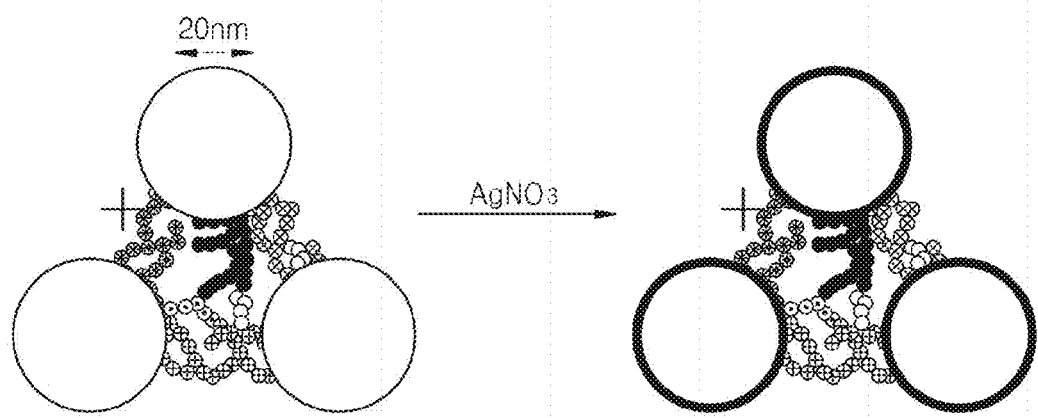
FIG. 5 is a diagram that illustrates a method of coating metal particles with silver by reducing the metal particles of the nucleic acid structure complex according to the exemplary embodiment.

FIG. 5 illustrates a method of coating metal particles with silver by reducing the metal particles of the nucleic acid structure complex according to the exemplary embodiment. Referring to FIG. 5, metal particles may be coated with silver through a chemical reduction process. An intensified Raman signal may be reproducibly obtained from the nucleic acid structure including the coated metal particles.

Figure 6:
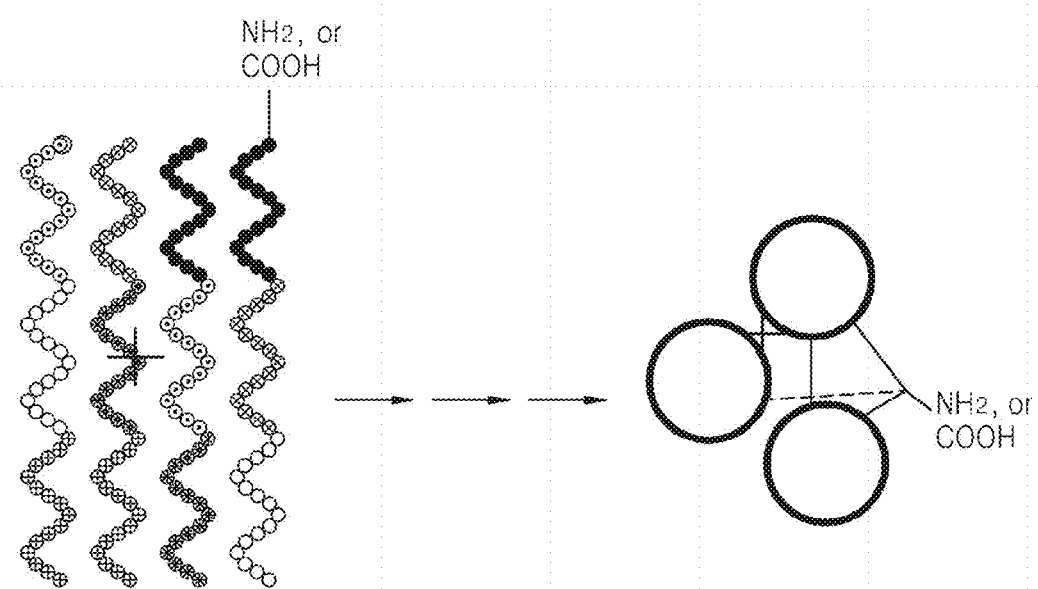
FIG. 6 is a diagram that illustrates an operation of preparing a nucleic acid structure complex including a functional group according to an exemplary embodiment.

FIG. 6 illustrates an operation of preparing a nucleic acid structure complex including a functional group according to an exemplary embodiment. Referring to FIG. 6, a nucleic acid structure complex including a functional group may be prepared by attaching a functional group to the nucleic acid constituting the nucleic acid structure complex. The functional group may be attached to any portion of the nucleic acid. The functional group may be attached to one end of the oligonucleotide. The nucleic acid structure complex may include the plurality of functional groups. The functional group may be for bonding a first material bondable to a target material to the nucleic acid structure complex. Examples of the functional group may be an amine group, a carboxyl group, or a thiol group. The functional group may protrude from a face or vertex of the nucleic acid structure complex.

Figure 7:
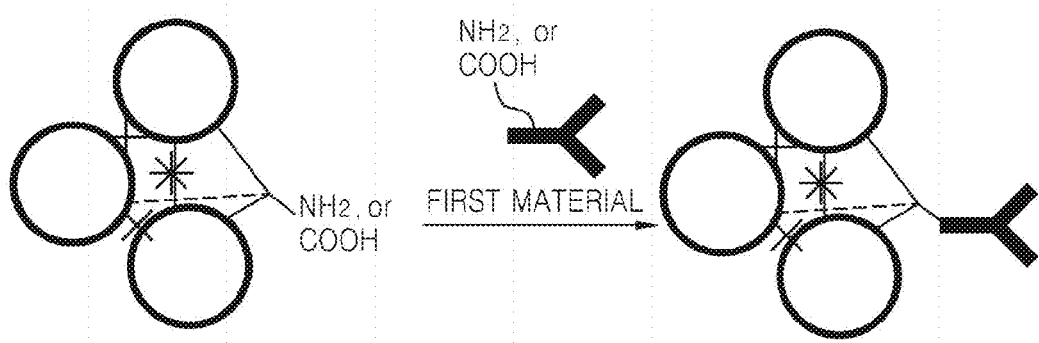
FIG. 7 is a diagram that illustrates bonding of a first material bondable to a target material and the nucleic acid structure complex including a functional group according to the exemplary embodiment.

FIG. 7 illustrates bonding of a first material bondable to a target material and the nucleic acid structure complex including a functional group according to the exemplary embodiment. Referring to FIG. 7, the nucleic acid structure complex including a functional group may be bonded to the first material bondable to a target material through the functional group. The functional group may be an amino group or a carboxyl group.

Figure 8:
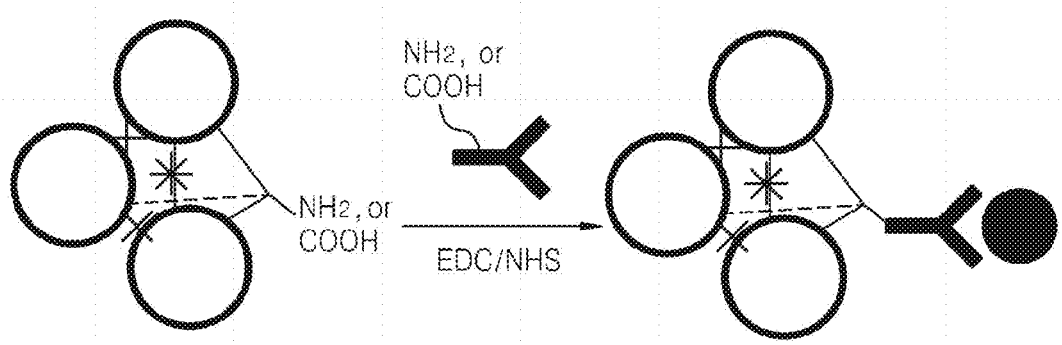
FIG. 8 is a diagram that illustrates bonding of a target material and the nucleic acid structure complex according to the exemplary embodiment.

FIG. 8 illustrates bonding of a target material and the nucleic acid structure complex according to the exemplary embodiment. Referring to FIG. 8, the nucleic acid structure complex including the first material bondable to a target material may be bonded to the target material. A Raman signal may be measured from the nucleic acid structure complex bonded to the target material.

Figure 9:
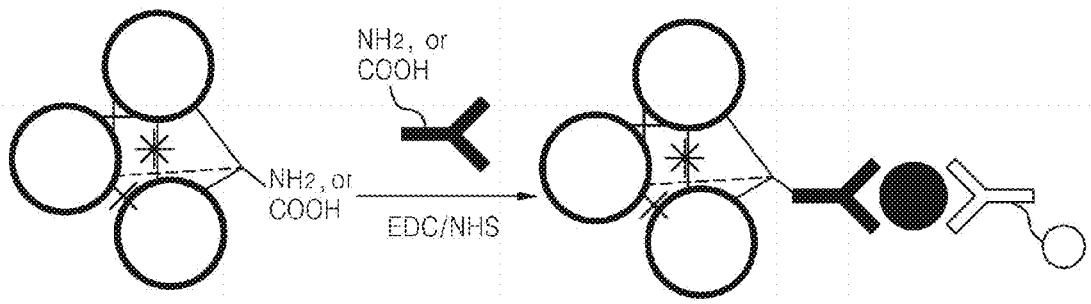
FIG. 9 is a diagram that illustrates bonding of the nucleic acid structure complex and a target material fixed to a support according to an exemplary embodiment.

FIG. 9 illustrates bonding of the nucleic acid structure complex and a target material fixed to a support according to an exemplary embodiment. Referring to FIG. 9, a target material may be fixed to a support by exposing the target material to the support including a second material bondable to the target material. The nucleic acid structure complex including the first material is exposed to the fixed target material and thus, the complex may be bonded to the target material. A Raman signal may be measured from the nucleic acid structure complex bonded to the target material.

Figure 10:
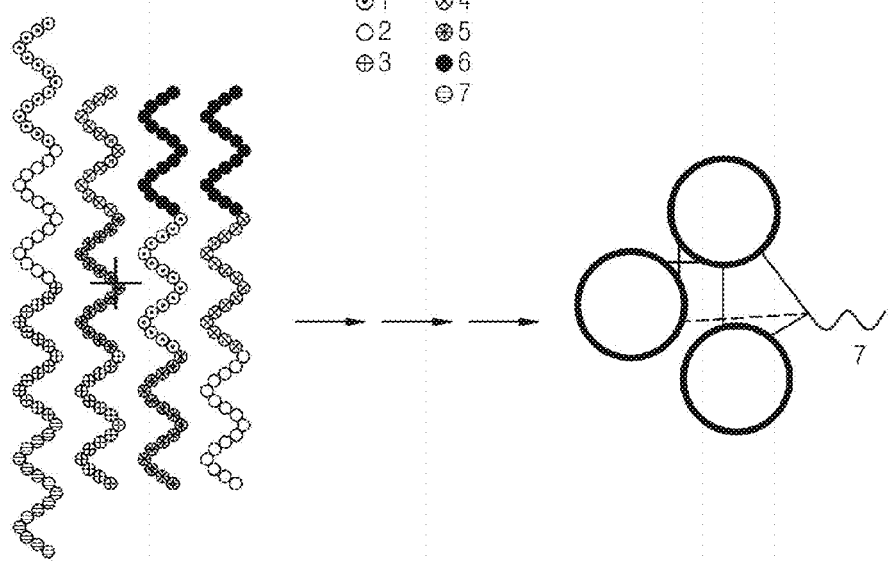
FIG. 10 is a diagram that illustrates an operation of preparing a nucleic acid structure complex including an oligonucleotide having a sequence complementary to a target nucleic acid according to an exemplary embodiment.

FIG. 10 illustrates an operation of preparing a nucleic acid structure complex including an oligonucleotide having a sequence complementary to a target nucleic acid according to an exemplary embodiment. Referring to FIG. 10, the nucleic acid constituting the nucleic acid structure complex may further include the oligonucleotide having a sequence complementary to a target nucleic acid 7. The oligonucleotide may be included in any portion of the nucleic acid. The oligonucleotide may be attached to one end of the nucleic acid. The nucleic acid structure complex may include an oligonucleotide having a sequence complementary to the plurality of target nucleic acids. The oligonucleotide having a sequence complementary to a target nucleic acid 7 may be for bonding the nucleic acid structure complex and the target nucleic acid included in the target material. The oligonucleotide having a sequence complementary to a target nucleic acid 7 may protrude from a face or vertex of the nucleic acid structure complex.

Figure 11:
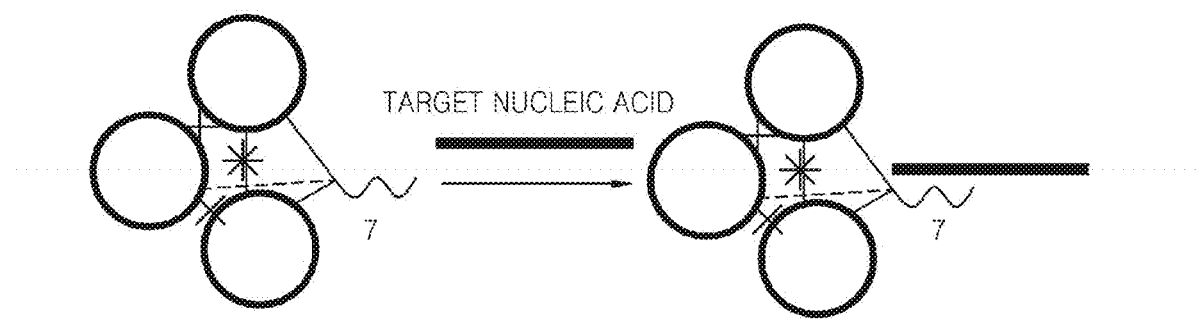
FIG. 11 is a diagram that illustrates bonding of the nucleic acid structure complex including an oligonucleotide having a sequence complementary to a target nucleic acid according to the exemplary embodiment and the target nucleic acid.

FIG. 11 illustrates bonding of the nucleic acid structure complex including an oligonucleotide having a sequence complementary to a target nucleic acid according to the exemplary embodiment and the target nucleic acid. Referring to FIG. 11, the oligonucleotide having a sequence complementary to a target nucleic acid 7 may be bonded to a portion of the target nucleic acid through a hybridization region. The target nucleic acid may be DNA or ribonucleic acid (RNA).

Figure 12:
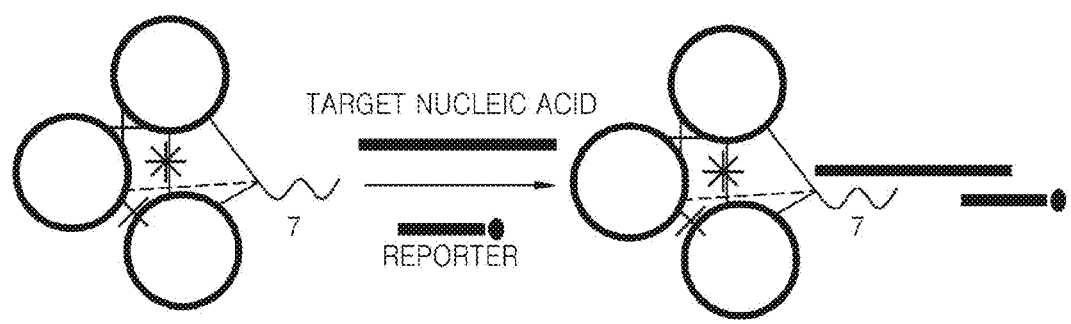
FIG. 12 is a diagram that illustrates bonding of the nucleic acid structure complex and a target nucleic acid fixed to a support according to an exemplary embodiment.

FIG. 12 illustrates bonding of the nucleic acid structure complex and a target nucleic acid fixed to a support according to an exemplary embodiment. Referring to FIG. 12, the nucleic acid structure complex is exposed to the support including a target nucleic acid and thus, the complex may be bonded to the target nucleic acid. A Raman signal may be measured from the nucleic acid structure complex bonded to the target nucleic acid.

EXAMPLE 1

Synthesis of Tetrahedron-Shaped DNA Nanostructure

Sequences of four single-stranded DNAs were designed in order to form a DNA polyhedron having a side with a length of about 7 nm and the four single-stranded DNAs are presented in Table 1. Sequences of oligonucleotide portions in the four sequences were listed by SEQ ID NO: 1 to SEQ ID NO: 4. The four sequences have complementary sequences and each sequence has three hybridization regions. A Cy3 Raman dye was introduced into SEQ ID NO: 4 among the sequences of the DNAs. Disulfide, i.e. $(HS)_2$—$CH(CH_2)_5$— was functionalized at the 5' ends of SEQ ID NO: 1 to SEQ ID NO: 3.

TABLE 1

| SEQ ID NO: 1 | Disulfide-TCCCATGTGTCTCGTCGTAAATTATATCATTC GGACGTTCCAGCTTCCCTGTTAAGTTCTAC |
|---|---|
| SEQ ID NO: 2 | Disulfide-TTACGACGAGACACATGGGAACCGAACAATGT CGGAACGGCAGGCCAATGCTCACGGCGGAG |
| SEQ ID NO: 3 | Disulfide-GGAACGTCCGAATGATATAAACTCCGCCGTGA GCATTGGCCATGAAACTCCCAGCGAGCAGC |
| SEQ ID NO: 4 | Disulfide-GCCGTTCCGACATTGTTCGGAGTAGAACTTA/ iCy3/ACAGGGAAGCAGCTGCTCGCTGGGAGTTCAT |

About 1 μl of each four 10 μM DNA was introduced and a buffer was added thereto to obtain about 100 μl. The composition of the buffer was 20 mM Tris (pH 7.6), 2 mM ethylenediaminetetraacetic acid (EDTA), and 12.5 mM MgCl$_2$. The temperature of the DNA mixture was maintained at about 95° C. for about 5 minutes by using a Thermocycler, and then, the temperature was decreased to about 4° C. Synthesis of a DNA nanostructure was confirmed by using a gel. A sample was put into a 5% Tris-borate-EDTA (TBE) gel and electrophoresis was performed at about 70 V for about 1 hour. Then, the sample was dyed with SYBR green to be identified. The DNA SEQ ID NOs added to each sample are listed in Table 2.

TABLE 2

Figure 13:
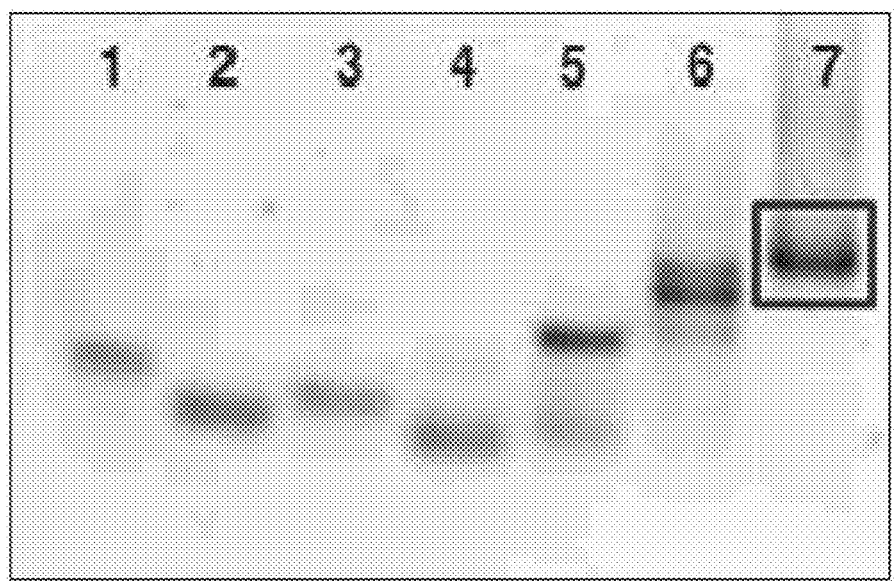
FIG. 13 is an image that illustrates the results of identifying a synthesized nucleic acid structure by using a gel.

| | Lane of FIG. 13 | | | | | | |
|---|---|---|---|---|---|---|---|
| | 1 | 2 | 3 | 4 | 5 | 6 | 7 |
| DNA SEQ ID NO: added | 1 | 2 | 3 | 4 | 1 and 2 | 1, 2, and 3 | 1, 2, 3, and 4 |

FIG. 13 illustrates the results of identifying a synthesized nucleic acid structure by using a gel. Referring to FIG. 13, it was confirmed that a DNA nanostructure was prepared when all the four DNA sequences were added.

EXAMPLE 2

Bonding of DNA Nanostructure and Gold Particles

Figure 14:
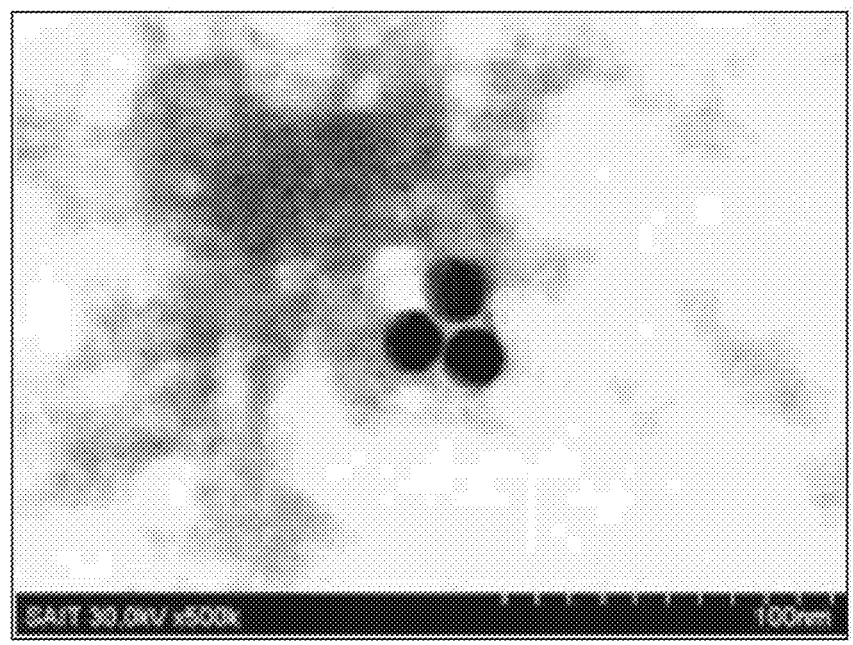
FIGS. 14 and 15 are images that illustrate the results of identifying nucleic acid structure complexes by using a scanning transmission electron microscope (STEM)
Figure 15:
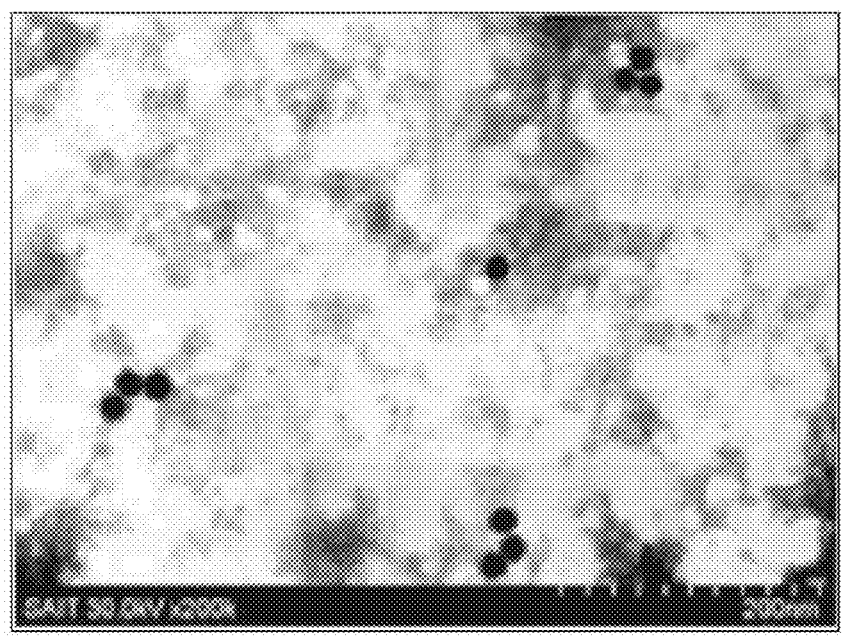

Freeze-dried DNA functionalized with 5'-disulfide was reduced by being reacted in about 400 μl of a 3% Tris(2-chloroethyl) phosphate (TCEP) solution. About 3 μl of 0.1 μM DNA nanostructures of Example 1 and about 1.2 ml of 1 nM gold particles having a particle diameter of about 20 nm were mixed and then stirred at room temperature overnight. Thereafter, the mixture thus obtained was observed with a scanning electron microscope (SEM), specifically UHR-SEM (S-5500). FIGS. 14 and 15 illustrate the results of identifying nucleic acid structure complexes by using a scanning transmission electron microscope (STEM). Referring to FIGS. 14 and 15, gold particles were bonded to the DNA nanostructures.

EXAMPLE 3

Coating Gold Particles with Silver

About 25 μl of a gold particle solution and a 1 mM AgNO$_3$ solution were reacted at room temperature for about 3 hours in the presence of about 10 μl of 1% poly-N-vinyl-2-pyrrolidone as a stabilizer and about 5 μl of 0.1 M L-sodium ascorbate as a reducing agent. The solution was dissolved in 0.3 M phosphate buffered saline (PBS). A volume of the 1 mM AgNO$_3$ solution was set as 0 μl, about 3 μl, about 5 μl, and about 7 μl to perform reactions, respectively. Then, ultraviolet and visible absorption spectrums (UV-VIS) were measured for the solutions thus obtained and the results thereof are presented in Table 3.

TABLE 3

| 1 mM AgNO$_3$ | Maximum wavelength (nm) |
|---|---|
| 0 μl | 525 |
| 3 μl | 509 |

TABLE 3-continued

| 1 mM AgNO$_3$ | Maximum wavelength (nm) |
|---|---|
| 5 μl | 506 |
| 7 μl | 495 |

EXAMPLE 4

SERS Measurement

Figure 16:
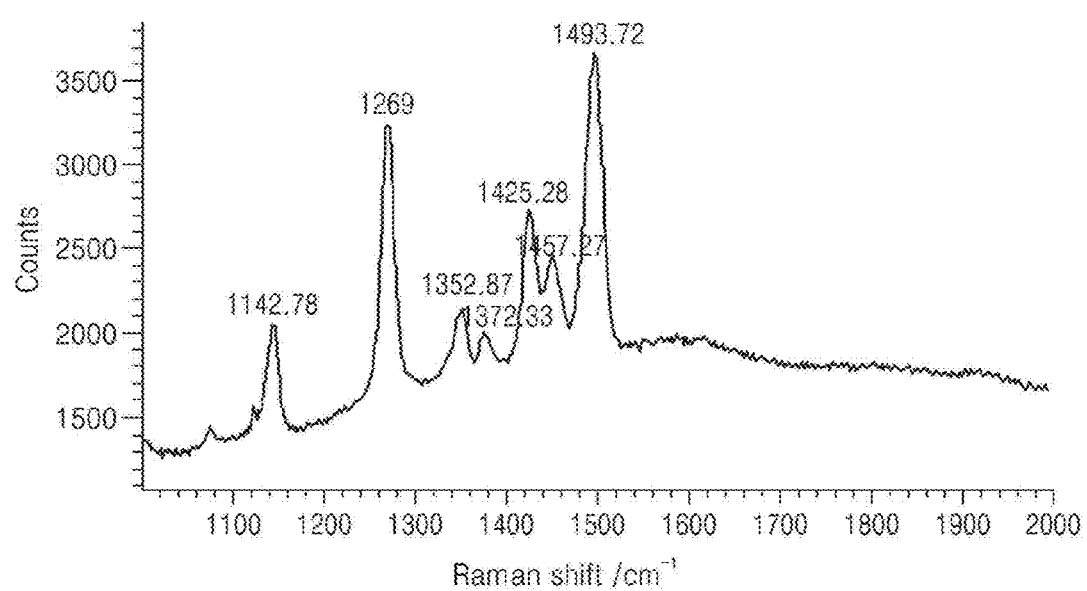
FIGS. 16 and 17 are graphs that illustrate the results of SERS spectrums measured by using a sample and a control group, respectively.
Figure 17:
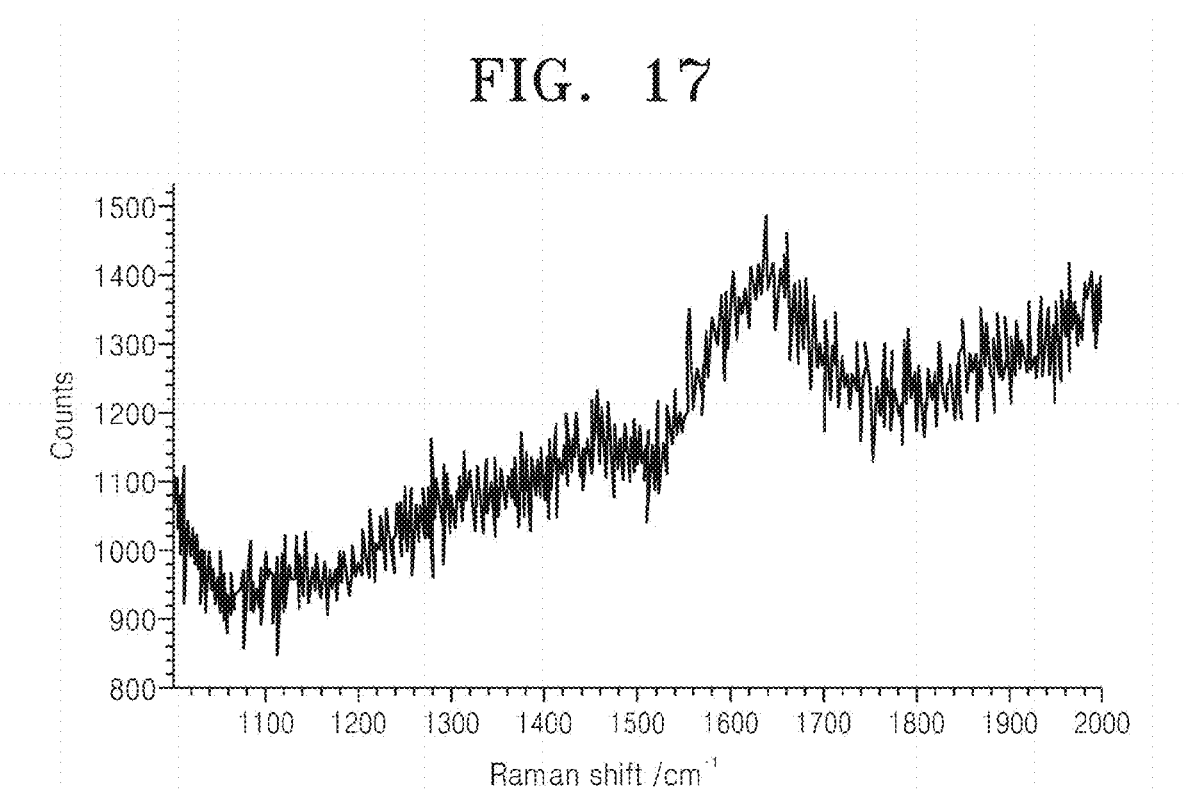

About 1.5 μl droplets of a sample and a control group were added to silicon samples and Raman scattering was measured. The control group was a sample to which a Raman dye was not added. Specifically, the measurements were performed by using an inVia-model instrument (Renishaw plc) with a 514 nm excitation laser at a laser power of 100% for an accumulation time of about 1 second and at 20× magnification. FIGS. 16 and 17 illustrate the results of SERS spectrums measured by using a sample and a control group, respectively. Referring to FIG. 16, the Raman spectrum of the sample showed relatively sharp peaks. In contrast, as illustrated in FIG. 17, the Raman spectrum of the control group did not show sharp peaks.

EXAMPLE 5

Generation of a Plurality of SERS by Introducing a Plurality of Raman-Active Molecules into Nucleic Acid Structure Complex A DNA nanostructure was synthesized in the same manner as in Example 1 except that a Cy3 Raman dye was introduced into sequence number 4 in the sequences of four single-stranded DNAs that were used in Example 1, in order to prepare a nucleic acid structure complex having only the Cy3 Raman dye introduced therein. Thereafter, gold particles were bonded to the synthesized DNA nanostructure in the same manner as in Examples 2 and 3, and the gold particles were coated with silver.

A DNA nanostructure was synthesized in the same manner as in Example 1 except that a Cy3 Raman dye was not introduced into sequence number 4 in the sequences of four single-stranded DNAs that were used in Example 1, but a FAM Raman dye was introduced into sequence number 3, in order to prepare a nucleic acid structure complex having only the FAM Raman dye introduced therein. Thereafter, gold particles were bonded to the synthesized DNA nanostructure in the same manner as in Examples 2 and 3, and the gold particles were coated with silver.

A DNA nanostructure was synthesized in the same manner as in Example 1 except that a FAM Raman dye was further introduced into sequence number 3 in the sequences of four single-stranded DNAs that were used in Example 1, in order to prepare a nucleic acid structure complex having both the FAM Raman dye and the Cy3 Raman dye introduced therein. Thereafter, gold particles were bonded to the synthesized DNA nanostructure in the same manner as in Examples 2 and 3, and the gold particles were coated with silver. Then, Raman signals of the three nucleic acid structure complexes were measured in the same manner as in Example 4.

Figure 18A:
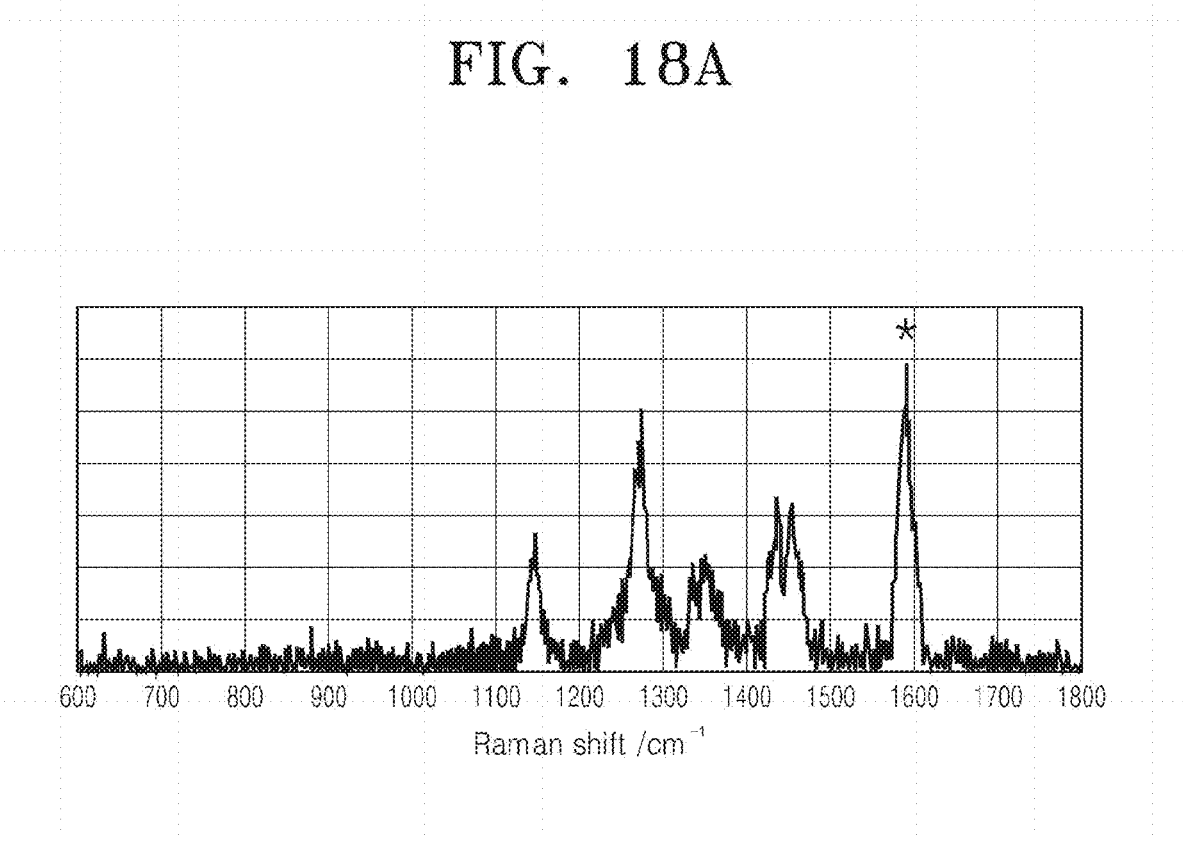
FIGS. 18A to 18C illustrate results of SERS spectrums of samples measured by using nucleic acid structure complexes.
Figure 18B:
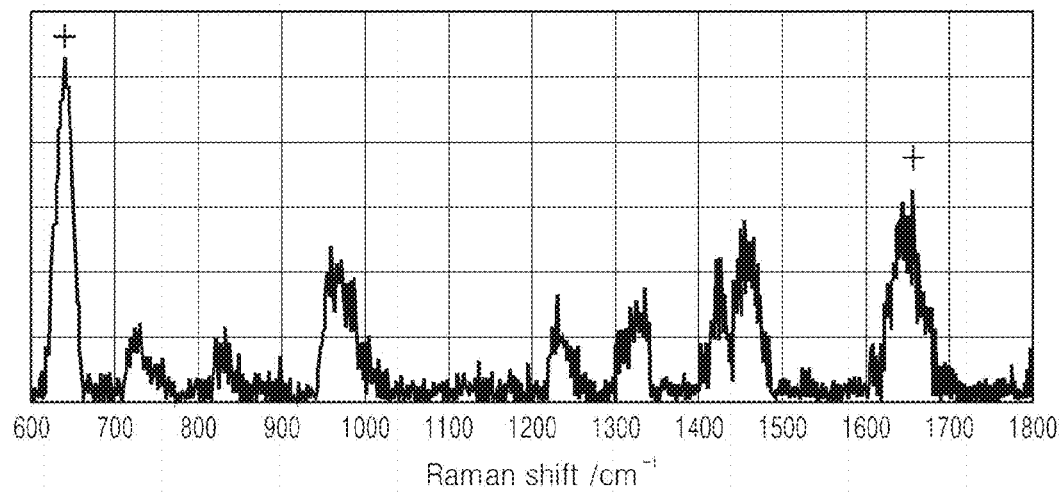
Figure 18C:
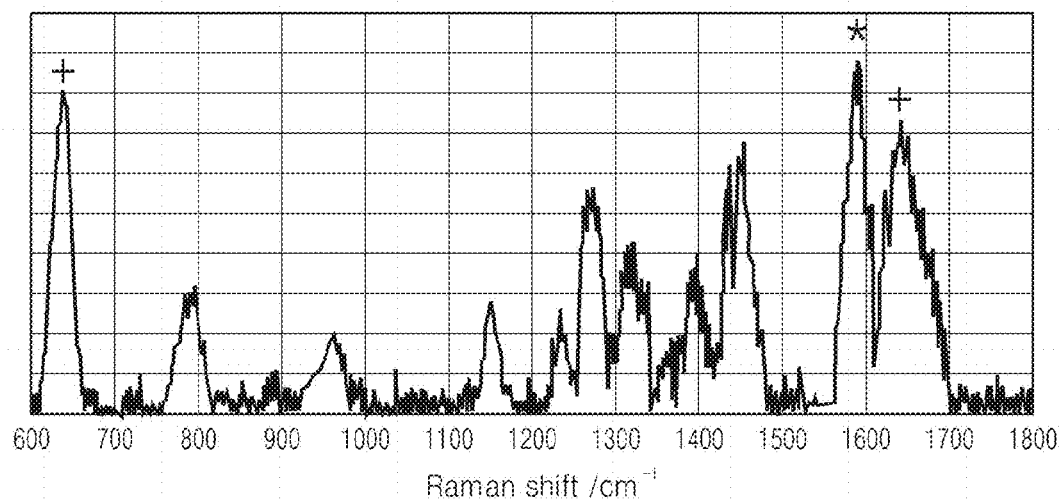

FIGS. 18A to 18C illustrate results of SERS spectrums of samples measured by using nucleic acid structure complexes. As illustrated in FIG. 18A, a Cy3 Raman signal was identified at about 1590 cm$^{-1}$, and FAM Raman signals were identified at about 636 cm$^{-1}$ and about 1642 cm$^{-1}$ as illustrated in FIG. 18B. As illustrated in FIG. 18C, Raman signals for the case of using both Cy3 and FAM were identified at about 636 cm$^{-1}$, about 1590 cm$^{-1}$, and about 1642 cm$^{-1}$. Since the Raman-active molecules such as Cy3 and FAM had narrow half widths, there was no overlap between the spectrums. Thus, it was confirmed that the Raman-active molecules such as Cy3 and FAM may be used as signal substances with various combinations. Therefore, as described in FIG. 4, it was confirmed that the nucleic acid structure complex including a plurality of Raman-active molecules may identify various target materials through the combination of the Raman-active molecules. For example, in a case where n Raman-active molecules are used, $2^{n-1}$ target materials may be identified.

According to an aspect of a nucleic acid structure complex, the nucleic acid structure complex may be used for reproducible Raman spectroscopy.

According to an aspect of a method of preparing a nucleic acid structure complex, a reproducible Raman signal detection material may be prepared.

According to an aspect of a method of detecting a target material, reproducible Raman spectroscopy may be performed. Also, various target materials may be analyzed.

While the present invention has been particularly shown and described with reference to exemplary embodiments thereof, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A nucleic acid structure complex comprising:
multiple nucleic acids hybridized to one another at a plurality of double stranded hybridization regions and configured as a polyhedron comprising six or more edges and four or more vertices;
at least two metal particles, each attached to a different vertex of the polyhedron;
a Ramen-active molecule attached to an edge of the polyhedron located between the vertices to which the metal particles are attached; and
at least a portion of the edges of the polyhedron are provided by double stranded regions of the nucleic acid.

2. The nucleic acid structure complex of claim 1, wherein the polyhedron is a tetrahedron, an octahedron, a dodecahedron, a trigonal bipyramid, or a bipyramid.

3. The nucleic acid structure complex of claim 1, wherein the nucleic acid structure complex further comprises a linker compound, and the metal particles are attached to the vertices by the linker compound.

4. The nucleic acid structure complex of claim 1, wherein the metal particles are Au (gold), Ag (silver), Cu (copper), Na (sodium), Al (aluminum), Cr (chromium), Pt (platinum), Ru (ruthenium), Pd (palladium), Fe (iron), Co (cobalt), Ni (nickel), or a combination thereof.

5. The nucleic acid structure complex of claim 1, wherein the metal particles are chemically reduced or subjected to laser ablation.

6. The nucleic acid structure complex of claim 1, wherein the Raman-active molecule comprises cyanine, fluorescein, rhodamine, NBD (7-nitrobenz-2-oxa-1,3-diazole), phthalic acid, terephthalic acid, isophthalic acid, cresyl fast violet, cresyl blue violet, brilliant cresyl blue, para-aminobenzoic acid, erythrosine, biotin, digoxigenin, phthalocyanine, azomethine, xanthine, N,N,-diethyl-4-(5'-azobenzotriazolyl) -phenylamine, aminoacridine, or the nucleic acid structure complex comprises a combination thereof.

7. The nucleic acid structure complex of claim 1, further comprising a material formed of organic molecules, inorganic molecules, or biomolecules on a surface of the metal particle.

8. The nucleic acid structure complex of "claim 1, wherein a plurality of the edges of the polyhedron comprise a different Raman active molecule".

9. The nucleic acid structure of claim 1 wherein the metal particles are silver-coated gold particles.

10. A method of preparing a nucleic acid structure complex of claim 1, the method comprising:
providing one or more oligonucleotides comprising one or more pairs of complementary nucleotide sequences;
hybridizing the complementary nucleotide sequences of the one or more oligonucleotides to form a polyhedron comprising six or more edges and four or more vertices, wherein at least a portion of the edges of the polyhedron are provided by double stranded regions of the nucleic acid; and
attaching at least two metal "particles, each to a different vertex,"and at least one Ramen- active molecule to at least one edge located between the vertices to which the metal particles are attached to provide the nucleic acid structure complex.

11. A method of detecting a target material, the method comprising:
exposing a nucleic acid structure complex of claim 1 to a sample comprising a target "material, wherein the nucleic acid structure complex comprises a targeting moiety that specifically binds to a target material; and"
detecting a Raman signal from the nucleic acid structure complex using Raman spectroscopy, wherein detection of a Raman signal indicates the presence of the target material in the sample.

12. The method of claim 11, wherein the method further comprises, after exposing the nucleic acid structure complex to the sample, separating the nucleic acid structure complex bound to the target material from unbound nucleic acid structure complex, and detecting nucleic acid structure complex bound to the target material by a Raman signal.

13. The method of claim 11, "wherein the targeting moiety comprises" a functional group that binds a target material or a sequence complementary to "target material comprising a nucleic acid sequence".

14. The method of claim 13, further comprising exposing the nucleic "acid structure complex comprising a sequence complementary to a target material comprising a nucleic acid sequence" to a sample comprising the "target nucleic acid sequence".

15. The method of "claim 11, wherein the targeting material comprises" a first material that specifically binds a target material.

16. The method of claim 15, wherein the first material is a protein or an antibody.

17. The method of claim 11, further comprising exposing a sample comprising a target material to a support comprising a second material, wherein the second material specifically binds to the target material.

* * * * *